(12) United States Patent
Houston et al.

(10) Patent No.: US 7,721,767 B2
(45) Date of Patent: May 25, 2010

(54) METHOD OF DETERMINING THE HELIX ANGLE OF A HELICAL FORMATION FOR A CONDUIT

(75) Inventors: John Graeme Houston, Central Scotland (GB); Robert Gordon Hood, Perth & Kiwross (GB); Peter Arno Stonebridge, Tayside (GB); Allan Thomson, Strathclyde (GB)

(73) Assignee: Tayside Flow Technologies Ltd. (GB)

( * ) Notice: Subject to any disclaimer, the term of this patent is extended or adjusted under 35 U.S.C. 154(b) by 1057 days.

(21) Appl. No.: 10/516,875

(22) PCT Filed: Dec. 13, 2002

(86) PCT No.: PCT/GB02/05646

§ 371 (c)(1),
(2), (4) Date: Aug. 9, 2005

(87) PCT Pub. No.: WO03/103540

PCT Pub. Date: Dec. 18, 2003

(65) Prior Publication Data

US 2006/0047334 A1    Mar. 2, 2006

(30) Foreign Application Priority Data

Jun. 5, 2002    (WO)    .................... PCT/GB02/02580

(51) Int. Cl.
*F15D 55/00*    (2006.01)

(52) U.S. Cl. ........................................ 138/39; 138/178

(58) Field of Classification Search .................... 138/39, 138/37, 110, 108, 172, 178, 177, 176, 106, 138/129, 150, 154; 72/74, 370.19, 59; 251/126
See application file for complete search history.

(56) References Cited

U.S. PATENT DOCUMENTS

| | | | |
|---|---|---|---|
| 3,313,577 A | 4/1967 | Edmund | |
| 4,629,458 A | 12/1986 | Pinchuk | |
| 6,514,284 B1 | 2/2003 | Cheng | |
| 6,776,194 B2 * | 8/2004 | Houston et al. | ................ 138/39 |
| 2003/0225453 A1 | 12/2003 | Murch | |

FOREIGN PATENT DOCUMENTS

| | | | |
|---|---|---|---|
| DE | 100 56 673 A | | 5/2002 |
| EP | 1 254 645 A | | 11/2002 |
| GB | 409 528 A | | 5/1934 |
| GB | 2 369 797 A | | 6/2002 |
| GB | 2 373 058 A | | 9/2002 |
| WO | WO 00/38591 | * | 6/2000 |
| WO | WO 00 38591 A | | 7/2000 |
| WO | 0189419 A1 | | 11/2001 |

* cited by examiner

*Primary Examiner*—Nicholas D Lucchesi
*Assistant Examiner*—Pritesh Patel
(74) *Attorney, Agent, or Firm*—DeMont & Breyer, LLC

(57) ABSTRACT

A Method of Determining the Helix Angle of a Helical Formation for a Conduit. A method of determining the helix angle of a helical formation (4) within a conduit (1). The method includes specifying the internal dimensions of the conduit (1) and an intended fluid mass flow through the conduit (1). The helix angle is determined from the pressure drop and the turbulent kinetic energy for a conduit (1) having the specified internal dimensions and intended fluid mass flow.

6 Claims, 1 Drawing Sheet

METHOD OF DETERMINING THE HELIX ANGLE OF A HELICAL FORMATION FOR A CONDUIT

Figure 1:
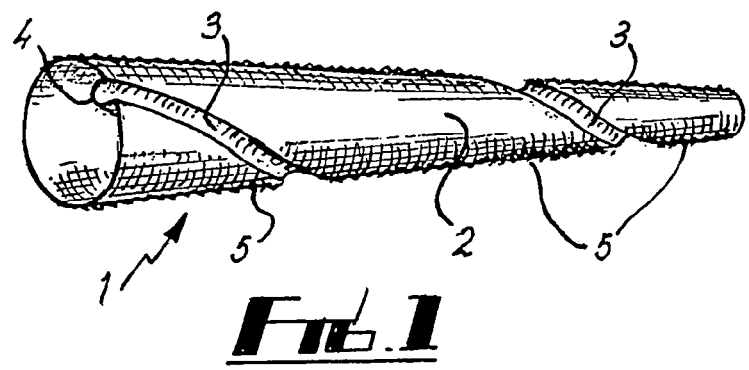

The invention relates to a method of determining the helix angle of a helical formation for a conduit, and in particular, but not solely, for blood flow tubing.

A number of documents have proposed using helical formations in conduits to encourage a desired flow pattern of a fluid within the conduit. Such helical formations have been proposed for a wide variety of applications, including pipelines and blood flow tubing. The purpose of the helical formations is generally to generate spiral flow of the fluid within the conduit to reduce turbulence and dead spots within the conduit.

Although the use of helical formations has been proposed as beneficial to fluid flow in conduits by helping to generate spiral fluid flow patterns, there is little or no information on the physical characteristics or design of the helical formation that is required to create a suitable spiral flow pattern. Clearly, some designs of helical formations will be ineffective at creating spiral flow and others will not create a beneficial spiral flow. For example, helical formations having a high helix angle may tend to create turbulence rather than spiral flow due.

In accordance with a first aspect of the present invention, there is provided a helical formation for a conduit, the helical formation defining at least a portion of a helix, the angle of the helix defined by the helical formation being determined from the internal dimensions of the conduit, the fluid mass flow of the conduit, the pressure drop along the conduit and the turbulent kinetic energy within the conduit.

In accordance with a second aspect of the present invention, there is provided a method of determining the helix angle of a helical formation for a conduit, the method comprising specifying the internal dimensions of the conduit and an intended fluid mass flow through the conduit, and determining the helix angle from the pressure drop and the turbulent kinetic energy for a conduit having the specified internal dimensions and intended fluid mass flow.

The terms "helical", "helix" and "spiral" as used herein cover the mathematical definition of helical and any combination of the mathematical definitions of helical and spiral.

Typically, the pressure drop and the turbulent kinetic energy are non-dimensionalised before the helix angle is determined.

Preferably, the helix angle is determined as the helix angle at which the non-dimensionalised pressure drop and the non-dimensionalised turbulent kinetic energy are substantially equal. However, the helix angle could be determined as a helix angle at which the non-dimensionalised pressure drop and the non-dimensionalised turbulent kinetic energy are not equal, depending on the type of conduit, the fluid and/or the application.

The helical formation may have a helix angle of between 5° and 50°. For example, the helical formation may have a helix angle of about 8°, particularly but not exclusively in relation to arterial flow in leg arterial grafts.

Typically, the fluid to be carried by the conduit comprises a liquid. The fluid may be solely a liquid, a liquid mixed with a particulate solid, or a liquified solid. For example, where the conduit is a blood vessel, the liquid is blood.

Typically, the helical formation may effect a rotational flow of fluid within the conduit, in use. The rotational flow may comprise a helical and/or spiral flow component.

Preferably, the helical formation may comprise an elongate member. Typically, the elongate member comprises an inwardly extending portion.

In one example of the invention, the helical formation may be in the form of an insert adapted to be mounted permanently or temporarily within the conduit.

In another example of the invention, the helical formation may be an integral part of the conduit and may be formed, for example, by a deformation of a side wall of the conduit. The helical formation may effect helical and/or spiral flow in such a fashion as to eliminate or reduce turbulence and/or eliminate or reduce dead flow regions in the conduit. The helix angle to achieve such flow will depend on such factors as diameter of the conduit, longitudinal and rotational velocity of the fluid, and the viscosity and other characteristics of the fluid.

The conduit may comprise tubing. For example, the conduit may comprise artificial or natural blood flow tubing, such as a vascular graft or a blood vessel, respectively. The tubing may be used in blood treatment or delivery equipment, for example a heart-lung machine, dialysis equipment or a giving set. The tubing may also be used in industrial equipment, for example hoses, pipes or fire hoses.

Alternatively, the conduit may comprise a stent. Stents, for example made of mesh, expanded sheet or tube or wire spring type, are inserted into blood vessels to provide mechanical support and prevent collapse of the blood vessel. A structure according to the present invention could be placed inside or outside the blood vessel to impose, maintain and/or reinforce a flow guiding formation through the blood vessel.

The invention may also be utilised for stent grafts. That is, a combination of stent and graft.

Flow configuration through a conduit may, in general, be measured using such techniques as magnetic resonance imaging (MRI) and/or Döppler ultrasound, and the flow guiding formation may be modified accordingly until a desired flow configuration is achieved. Initial design of flow configuration may be by mathematical modelling or by trial and error, with modification as described above.

The conduit may be a flexible conduit, such as a tube or hose, or a substantially rigid conduit, such as a metal pipe or a pipeline.

Figure 2:
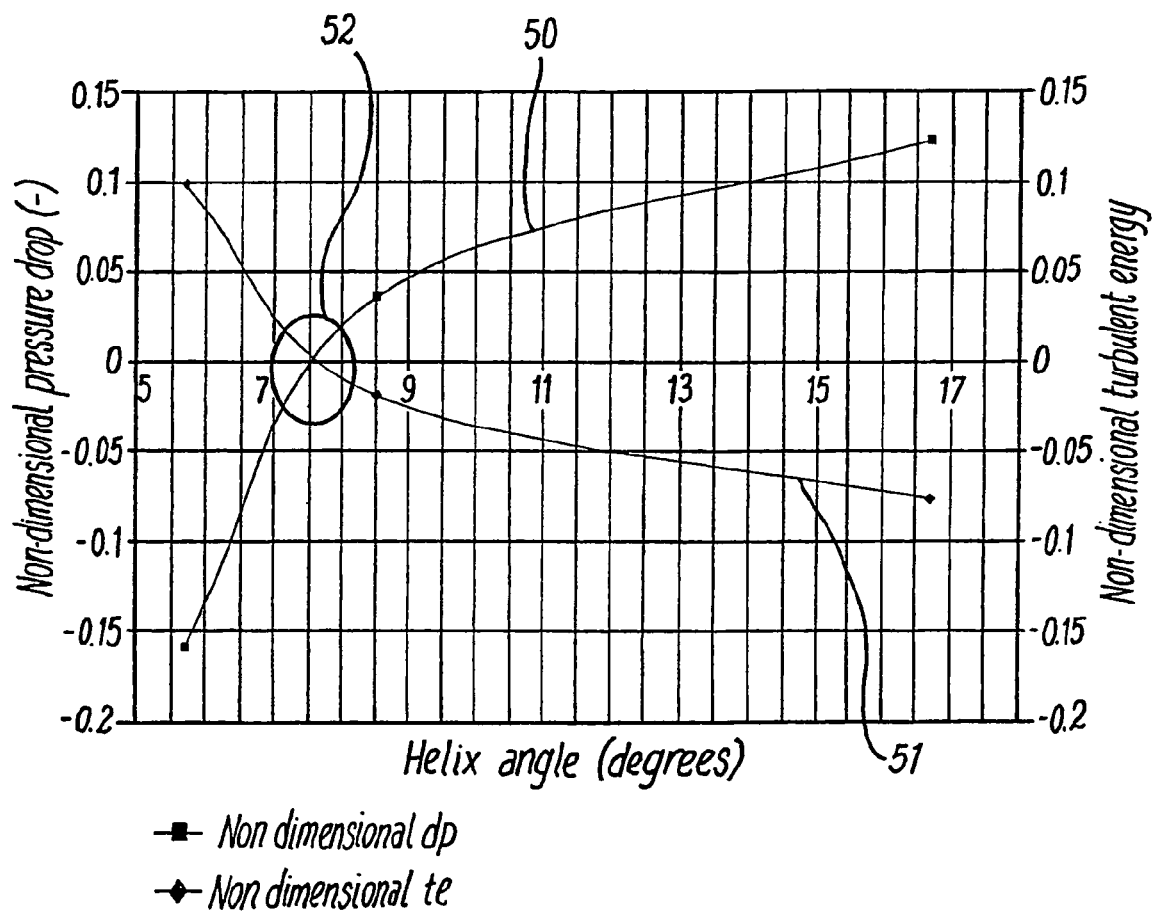

Examples of a method of determining the helix angle of a helical formation will now be described with reference to the accompanying drawings, in which:

FIG. 1 is a perspective view of an arterial graft having a helical formation; and FIG. 2 is a graph of helix angle versus pressure drop and helix angle versus turbulent kinetic energy for the arterial graft.

FIG. 1 is a perspective view of an arterial graft 1 for implantation in the human or animal body. The graft 1 is fabricated from a knitted or woven polyester material. However, any suitable flexible material could be used, such as a spun polyurethane multi-monofilament or a PTFE extrusion.

The graft 1 is in the form of a tube 2 that has a deformation 3 in the side wall of the tube 2 so that the deformation 3 extends inwardly generally towards the longitudinal axis of the tube 2 to form a helical formation 4 on the internal surface of the tube 2. The tube is also crimped to form circumferential ridges 5 along the length of the tube 2. The circumferential ridges help to provide radial strength to the tube 2 to minimise the risk of the graft collapsing during implantation and subsequently during use.

The helical formation 4 is intended to promote a rotational flow pattern to blood passing through the graft 1, in use. It is believed that rotational flow has beneficial effects in reducing the effect of and helping to prevent arterial diseases, by reducing turbulent flow and reducing dead spots within the flow.

The inventors have found that the choice of the helix angle of the helical formation 4 is important in minimising turbulent flow and dead spots within the flow. The inventors have also found that for a conduit having given internal dimensions and a particular helical flow formation that is intended to carry a given mass flow, the optimum helix angle can be determined from the pressure drop along the conduit and the turbulent kinetic energy in the conduit.

In addition, the inventors have found that, in order to maintain a given mass flow in a given conduit, with a particular helical flow formation, the pressure drop increases as the helix angle increases and the turbulent kinetic energy decreases as the helix angle increases. Hence, the choice of helix angle is a compromise between minimising pressure drop and minimising turbulent kinetic energy. If the pressure drop and turbulent kinetic energy are non-dimensionalised using conventional mathematical techniques, the curves of helix angle versus non-dimensionalised pressure drop and helix angle versus turbulent kinetic energy can be plotted on the same graph. A curve 50 of helix angle versus non-dimensionalised pressure drop and a curve 51 of helix angle versus non-dimensionalised turbulent kinetic energy for an arterial graft are shown in FIG. 2. These curves 50, 51 were obtained from measuring pressure drop and turbulent kinetic energy in the arterial graft 1 using conventional techniques. The curves 50, 51 show that at the region 52, the curves intersect and this intersection occurs at a helix angle of approximately 8°.

By also analysing flow in the graft 1 using conventional magnetic resonance imaging techniques it was found by trial and error that the optimum helix angle for the graft 1 for the given mass flow was also approximately 8°. Hence, the optimum helix angle for the graft 1 occurs at approximately when the non-dimensionalised pressure drop is approximately equal to the non-dimensionalised turbulent kinetic energy.

Although in the example described above the helix angle is determined as the angle at which the non-dimensionalised pressure drop and turbulent kinetic energy are substantially equal, there may be situations in which the helix angle is selected so that the non-dimensionalised pressure drop and turbulent kinetic energy are not equal. This may situation may arise if, for example, a lower turbulent kinetic energy is required and it is decided to tolerate a higher pressure drop to obtain a lower turbulent kinetic energy. Similarly, if a low pressure drop is more important than turbulent kinetic energy, a higher turbulent kinetic energy may be tolerated to obtain a lower pressure drop. Hence, the choice of the helix angle can be chosen according to the particular application, and different applications may have different requirements.

In the example described above, the helix angle of the helical formation is determined for the graft 1. However, the same technique can be used for other conduits where it is desired to use a helical formation to alter the flow pattern of fluid the conduit. For example, the same technique could also be used to determine the helix angle for a helical formation for use in a stent, or indeed any other medical application involving the flow of a fluid through a tube.

The present invention is also suitable for industrial applications. Helical formations may also be used in conduits such as tubes to create improved efficiency through quicker transfer of fluid and reduced energy use or a reduction in pressure gradient along the tube allowing lower pressures within the tube to deliver a specific end conduit pressure/flow rate. Helical formations could be used to effect a reduction in turbulence, thereby reducing vibration, noise, and/or fatigue in a conduit, which in pumps could allow for reduced pump power consumption. Helical formations may also be used to allow further penetration or more accurate distribution patterns of fluid exiting a conduit, for example from a hose pipe for domestic use or from a fire hose. The invention will also be of benefit to industries where slurries or suspensions are transported through conduits, for example food producers or distributors involved with soups, sauces and like products.

As with the example above of the graft 1, the optimum helix angle for these other types of conduits can be determined from the pressure drop and the turbulent kinetic energy. Therefore, the invention has the advantage of enabling the helix angle of a helical flow formation in a given size of conduit intended to carry a given fluid to be determined from the pressure drop and the turbulent kinetic energy in the conduit.

The invention claimed is:

1. A method of determining the helix angle of a helical formation for a conduit, the method comprising specifying the internal dimensions of the conduit and an intended fluid mass flow through the conduit, and determining the helix angle from the pressure drop and the turbulent kinetic energy for a conduit having the specified internal dimensions and intended fluid mass flow, wherein the pressure drop and the turbulent kinetic energy are non-dimensionalised before the helix angle is determined, and wherein the helix angle is determined as a helix angle at which the non-dimensionalised pressure drop and the non-dimensionalised turbulent kinetic energy are not equal.

2. A method according to claim 1, wherein the helix angle is determined as being between 5° and 50°.

3. A method according to claim 2, wherein the helix angle is determined as being between 5° and 20°.

4. A method according to claim 3, wherein the helix angle is determined as being substantially 8°.

5. A method according to claim 1, wherein the conduit is blood flow tubing.

6. A method according to claim 1, wherein the helical formation is for effecting a rotational flow of fluid within the conduit, in use.

* * * * *

UNITED STATES PATENT AND TRADEMARK OFFICE
CERTIFICATE OF CORRECTION

| | | |
|---|---|---|
| PATENT NO. | : 7,721,767 B2 | Page 1 of 1 |
| APPLICATION NO. | : 10/516875 | |
| DATED | : May 25, 2010 | |
| INVENTOR(S) | : Houston et al. | |

It is certified that error appears in the above-identified patent and that said Letters Patent is hereby corrected as shown below:

Title page, item (86) should read as follows:

(86) PCT No.: PCT/GB02/05646

§ 371 (c)(1),
(2), (4) Date: Aug. 4, 2005

Signed and Sealed this

Seventeenth Day of August, 2010

David J. Kappos
*Director of the United States Patent and Trademark Office*